United States Patent
Iwasaki et al.

(10) Patent No.: US 9,587,015 B2
(45) Date of Patent: Mar. 7, 2017

(54) ANTI-HUMAN CTGF ANTIBODY

(71) Applicant: ASTELLAS PHARMA INC., Tokyo (JP)

(72) Inventors: Shoji Iwasaki, Tokyo (JP); Ryuichi Moriya, Tokyo (JP); Masayasu Yoshino, Tokyo (JP); Koji Takakura, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/367,081

(22) PCT Filed: Dec. 21, 2012

(86) PCT No.: PCT/JP2012/083206
§ 371 (c)(1),
(2) Date: Jun. 19, 2014

(87) PCT Pub. No.: WO2013/094723
PCT Pub. Date: Jun. 27, 2013

(65) Prior Publication Data
US 2014/0343258 A1 Nov. 20, 2014

(30) Foreign Application Priority Data
Dec. 22, 2011 (JP) ................. 2011-281811

(51) Int. Cl.
| | |
|---|---|
| *A61K 39/395* | (2006.01) |
| *C12P 21/06* | (2006.01) |
| *C12P 21/04* | (2006.01) |
| *C12N 15/00* | (2006.01) |
| *C12N 5/00* | (2006.01) |
| *C07K 16/00* | (2006.01) |
| *C07H 21/00* | (2006.01) |
| *C07K 16/22* | (2006.01) |
| *C07K 14/475* | (2006.01) |
| *A61K 39/00* | (2006.01) |

(52) U.S. Cl.
CPC ............ *C07K 16/22* (2013.01); *C07K 14/475* (2013.01); *A61K 2039/505* (2013.01); *C07K 2317/24* (2013.01); *C07K 2317/41* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,492,129 | B1 | 12/2002 | Grotendorst |
| 6,562,618 | B1 | 5/2003 | Tamatani et al. |
| 6,596,541 | B2 | 7/2003 | Murphy et al. |
| 7,405,274 | B2 | 7/2008 | Lin et al. |
| 7,541,438 | B2 | 6/2009 | Tamatani et al. |
| 7,718,177 | B2 | 5/2010 | Grotendorst |
| 2002/0106629 | A1 | 8/2002 | Murphy et al. |
| 2003/0166011 | A1 | 9/2003 | Tamatani et al. |
| 2003/0180300 | A1 | 9/2003 | Grotendorst |
| 2004/0092450 | A1 | 5/2004 | Grotendorst et al. |
| 2004/0248206 | A1 | 12/2004 | Lin et al. |
| 2006/0223133 | A1 | 10/2006 | Tamatani et al. |
| 2010/0158907 | A1 | 6/2010 | Grotendorst et al. |
| 2010/0190838 | A1 | 7/2010 | Grotendorst |
| 2014/0073047 | A1 | 3/2014 | Lin et al. |

FOREIGN PATENT DOCUMENTS

| | | |
|---|---|---|
| CN | 1829740 A | 9/2006 |
| EP | 1 043 335 A1 | 10/2000 |
| JP | 2000-232884 A | 8/2000 |
| JP | 2002-532082 A | 10/2002 |
| JP | 2004-524841 A | 8/2004 |
| JP | 2007-525194 A | 9/2007 |
| WO | WO 99/33878 A1 | 7/1999 |
| WO | WO 2004/108764 A2 | 12/2004 |
| WO | WO 2007/066823 A1 | 6/2007 |
| WO | WO 2010/053751 A1 | 5/2010 |

*Primary Examiner* — Marianne P Allen
(74) *Attorney, Agent, or Firm* — Oblon, McClelland, Maier & Neustadt, L.L.P.

(57) ABSTRACT

Novel anti-human CTGF antibodies having excellent binding activity and/or neutralizing activity, as compared with conventional anti-human CTGF antibodies, are useful for treating various diseases in which human CTGF is involved in pathogenesis, including renal diseases such as chronic kidney disease and diabetic nephropathy.

25 Claims, No Drawings

ANTI-HUMAN CTGF ANTIBODY

CROSS REFERENCES TO RELATED APPLICATIONS

This application is a 371 of International Patent Application No. PCT/JP12/083206, filed on Dec. 21, 2012, and claims priority to Japanese Patent Application No. 2011-281811, filed on Dec. 22, 2011.

TECHNICAL FIELD

The present invention relates to a novel anti-human CTGF antibody. Specifically, the novel anti-human CTGF antibody of the present invention is an anti-human CTGF antibody having excellent binding activity and/or neutralizing activity, as compared with conventional anti-human CTGF antibodies.

BACKGROUND ART

CTGF (connective tissue growth factor) is a secreted protein rich in cysteine residues with a molecular weight of about 36 to 38 kDa, belonging to a CCN family (Non-Patent Document 1), and has been conventionally known to be induced by TGF-β that can be considered to be the most important growth factor in fibrosis (Non-Patent Document 2). Therefore, it is suggested that TGF-β induces CTGF and the induced CTGF promotes the fibrosis of organs or tissues, and it is believed that CTGF plays an important role in fibrosis, cell proliferation, metabolism of the extracellular matrix, angiogenesis, arteriosclerosis, and the like (Non-Patent Document 3).

It has become known that there are many domains present in CTGF, which interact with other factors. Among them, it is known that CTGF is coupled directly with TGF-β or BMP4 via von Willebrand C domain, and causes the promotion of TGF-β signaling or the inhibition of BMP signaling (Non-Patent Document 4).

It has become known that expression of CTGF is increased in various renal diseases (for example, chronic kidney disease, diabetic nephropathy, glomerulosclerosis, IgA nephropathy, focal segmental glomerulosclerosis, ANCA-related nephritis, acute progressive glomerulonephritis, chronic transplant nephropathy, nephrotic syndrome, lupus nephritis and membranoproliferative glomerulonephritis) (Non-Patent Document 5), and it has been reported that CTGF is deeply involved in fibrosis (Non-Patent Document 6).

In addition, it has been reported that CTGF is involved in various types of fibrosis (scleroderma, interstitial lung disease, pulmonary fibrosis diseases such as idiopathic pulmonary fibrosis, fibrosis caused by chronic hepatitis B or C, radiation-induced fibrosis, fibrosis caused by wound healing, and cardiac hypertrophy and fibrosis), vascular proliferative diseases, diabetic retinopathy, cancer, and the like, and thus, it can be thought that CTGF could be a new therapeutic target (Non-Patent Documents 7 and 8).

Therefore, if a monoclonal antibody which specifically binds to CTGF and has an activity inhibiting various actions of CTGF can be developed, the monoclonal antibody is expected to be useful for diagnosis, prevention or treatment of various diseases in which CTGF is involved in pathogenesis.

As an antibody showing an inhibitory function against human CTGF, which have been hitherto studied, human monoclonal antibodies M84 and M320 (Patent Document 1), CLN1 (Patent Document 2), a mouse monoclonal antibody CTGF-m2-1 (Patent Document 3), and the like have been reported. Among them, CLN1 has been investigated in most detail, and its effect has been identified in an interstitial pulmonary fibrosis model or a renal interstitial fibrosis model by unilateral ureteral ligation. CLN1 is studied in clinical trial (Phase II) as FG-3019.

However, it cannot be said that conventional antibodies have sufficient binding activity for CTGF, and have sufficiently strong neutralizing activity for CTGF from a viewpoint of therapeutic effectiveness.

In general, examples of the major factors defining the effective doses of the antibody pharmaceuticals include the binding activity or neutralizing activity which the antibody has for an antigen, and the amount of an antigen present in the body. However, it can be said that improvement of the binding activity or the neutralizing activity directly leads to reduction in the dose, and as a result, it is a very useful improvement, leading to reduction in the economic burden of a patient or medical cost.

For these reasons, it is essential to acquire an anti-human CTGF antibody having stronger binding activity or neutralizing activity than conventional antibodies for the purpose of using in prevention or treatment of various diseases, in which CTGF is involved in the pathogenesis.

RELATED ART

Patent Document

[Patent Document 1] JP-A-2000-232884
[Patent Document 2] WO2004/108764
[Patent Document 3] WO2007/066823

Non-Patent Document

[Non-Patent Document 1] D. M. Bradham et al., J. Cell Biol. 114:1285-1294 (1991)
[Non-Patent Document 2] A. Igarashi et al., Mol. Biol. Cell 4:637-645 (1993)
[Non-Patent Document 3] Blom I E et al., Matrix Biol. 21(6):473-82 (2002)
[Non-Patent Document 4] Abreu, et al., Nat. Cell. Biol. 4, 599-604 (2002)
[Non-Patent Document 5] Ito Y et al., Kidney Int. 53(4) 853-61 (1998)
[Non-Patent Document 6] Phanish M K et al., Nephron Exp Nephrol. 114(3) e83-92 (2010)
[Non-Patent Document 7] Shi-Wen X et al., Cytokine Growth Factor Rev. 19(2):133-44 (2008)
[Non-Patent Document 8] Jun J I et al., Nat Rev Drug Discov. 10(12):945-63 (2011)

DISCLOSURE OF INVENTION

Problem to be Solved by the Invention

An object of the present invention is to provide anti-human CTGF antibodies having excellent binding activity and/or neutralizing activity, as compared with conventional anti-human CTGF antibodies.

Means for Solving the Problems

The present invention includes the following invention as medically or industrially useful substances and methods.

[1] An anti-human CTGF antibody, comprising:
a heavy-chain variable region consisting of the amino acid sequence shown by SEQ ID NO: 10; and
a light-chain variable region consisting of the amino acid sequence shown by SEQ ID NO: 4.

[2] The anti-human CTGF antibody according to [1], wherein a heavy-chain constant region of the antibody is a human Igγ1 constant region.

[3] The anti-human CTGF antibody according to [1], wherein a light-chain constant region of the antibody is a human Igκ constant region.

[4] The anti-human CTGF antibody according to [1], wherein a heavy-chain constant region of the antibody is a human Igγ1 constant region, and a light-chain constant region of the antibody is a human Igκ constant region.

[5] The anti-human CTGF antibody according to [1], comprising:
a heavy chain consisting of the amino acid sequence shown by SEQ ID NO: 12; and
a light chain consisting of the amino acid sequence shown by SEQ ID NO: 8.

[6] A polynucleotide comprising a sequence that encodes the heavy-chain variable region of the antibody according to any one of [1] to [5].

[7] A polynucleotide comprising a sequence that encodes the light-chain variable region of the antibody according to any one of [1] to [5].

[8] An expression vector comprising the polynucleotide according to [6] and/or [7].

[9] A host cell transformed with the expression vector according to [8].

[10] The host cell according to [9], which is selected from the group consisting of the following (a) and (b):
(a) a host cell transformed with an expression vector comprising a polynucleotide comprising a sequence that encodes the heavy-chain variable region of the antibody according to any one of [1] to [5] and a polynucleotide comprising a sequence that encodes the light-chain variable region of the antibody; and
(b) a host cell transformed with an expression vector comprising a polynucleotide comprising a sequence that encodes the heavy-chain variable region of the antibody according to any one of [1] to [5], and an expression vector comprising a polynucleotide comprising a sequence that encodes the light-chain variable region of the antibody.

[11] A method for producing the anti-human CTGF antibody according to any one of [1] to [5], the method comprising expressing the anti-human CTGF antibody by culturing the host cell according to [9] or [10].

[12] An therapeutic agent for a disease in which human CTGF is involved in pathogenesis, comprising the antibody according to any one of [1] to [5].

[13] The therapeutic agent according to [12], wherein the disease is kidney disease.

[14] The therapeutic agent according to [13], wherein the kidney disease is chronic kidney disease or diabetic nephropathy.

[15] A method for preventing or treating a disease in which human CTGF is involved in pathogenesis, comprising administering the antibody according to any one of [1] to [5].

[16] The method according to [15], wherein the disease is kidney disease.

[17] The method according to [16], wherein the kidney disease is chronic kidney disease or diabetic nephropathy.

[18] The antibody according to any one of [1] to [5], for use in preventing or treating a disease in which human CTGF is involved in pathogenesis.

[19] The antibody according to [18], wherein the disease is kidney disease.

[20] The antibody according to [19], wherein the kidney disease is chronic kidney disease or diabetic nephropathy.

Effects of the Invention

According to the present invention, anti-human CTGF antibodies having excellent binding activity and/or neutralizing activity, as compared with conventional anti-human CTGF antibodies, are provided. The anti-human CTGF antibody of the present invention has a potent antifibrotic action by inhibiting the function of human CTGF, and is useful for prevention or treatment of various diseases, in which human CTGF is involved in pathogenesis. Further, the anti-human CTGF antibody of the present invention provides significant improvements in clinical applications such as reduction of dosage, extension of administration interval, improvement of the mode of administration (for example, a subcutaneous injection), and the like, and thus, greatly contributes to improvement in treatment effectiveness and patient compliance.

EMBODIMENTS FOR CARRYING OUT THE INVENTION

Hereinafter, the present invention will be described in detail.

The present inventors have made extensive studies on preparation of anti-human CTGF antibodies, and as a result, they have succeeded in producing anti-human CTGF antibodies having improved binding activity and excellent neutralizing activity as compared with conventional anti-human CTGF antibodies.

The basic structure of an antibody molecule is shared amongst all antibody classes, and is configured with a heavy chain having a molecular weight of 50000 to 70000 and a light chain having a molecular weight of 20000 to 30000. The heavy chain usually consists of a polypeptide chain comprising about 440 amino acids. Heavy chains have structures characteristic of different classes, and are called the γ, μ, α, δ and ε chains corresponding to IgG, IgM, IgA, IgD and IgE. Furthermore, IgG occurs as IgG1, IgG2, IgG3 and IgG4, and the corresponding chains are called γ1, γ2, γ3 and γ4, respectively. A light chain usually consists of a polypeptide chain comprising about 220 amino acids, two types of which, type L and type K, are known, and are called the λ and κ chains, respectively. Regarding the peptide configuration of the basic structure of an antibody molecule, two homologous heavy chains and two homologous light chains are bound via disulfide bonds (S—S bonds) and non-covalent bonds, and the molecular weight is 150000 to 190000. The two kinds of light chains are capable of pairing with any heavy chain. Each antibody molecule always consists of two identical light chains and two identical heavy chains.

There are four intrachain S—S bonds in a heavy chain (five bonds for μ and ε chains) and two in a light chain; one loop is formed per 100 to 110 amino acid residues, and this steric structure is alike among the loops, and is called a structural unit or domain. For both heavy chains and light chains, the amino acid sequence of the domain located at the N terminus thereof is not constant, even in a reference standard from the same class (subclass) of the same animal species, and this domain is called the variable region. Each of the domains is called a heavy-chain variable region ($V_H$) and a light-chain variable region ($V_L$), respectively. The amino acid sequence on the C-terminal side therefrom is nearly constant in each class or subclass, and is called a constant region (each of the domains is called $C_H1$, $C_H2$, $C_H3$ and $C_L$, respectively).

The antigenic determinant site of an antibody is configured with $V_H$ and $V_L$, and the binding specificity depends on the amino acid sequence of this site. On the other hand, biological activities such as binding to complements or various cells reflect the differences in the constant region structure among the various classes of Ig. The variability in the variable regions of the light chain and heavy chains is mostly limited to three small hypervariable regions existing in both chains, and these regions are called complementarity determining regions (CDRs; CDR1, CDR2 and CDR3 starting from the N-terminal side). The remaining portion of the variable region is called a framework region (FR) and is relatively constant.

The anti-human CTGF antibody of the present invention that the present inventors have succeeded in preparing is an anti-human CTGF antibody having the following characteristics.

An anti-human CTGF antibody comprising a heavy-chain variable region consisting of the amino acid sequence shown by SEQ ID NO: 10 and a light-chain variable region consisting of the amino acid sequence shown by SEQ ID NO: 4.

Specifically, the present inventors constructed antibodies using a human monoclonal antibody development technology, "VelocImmune" mouse [VelocImmune antibody technology; Regeneron Inc. (U.S. Pat. No. 6,596,541)], and screened the antibodies using tests for various biological activities and physical properties, thereby succeeding in identifying the anti-human CTGF antibody of the present invention. In the VelocImmune technology, transgenic mice in which the endogenous immunoglobulin heavy chain and light chain variable regions are replaced with the corresponding human variable regions are immunized with the antigen of interest (for example, human CTGF), and lymphatic cells are recovered from the mice that express antibodies. The lymphatic cells are fused with mouse myeloma cells to prepare hybridomas. The hybridoma cells are screened to identify hybridoma cells that produce those antibodies that specifically bind to the antigen of interest. The antibodies that are produced herein are antibodies having the variable regions of human antibodies and the constant regions of mouse antibodies (also referred to as chimeric antibodies). Then, if the antibody that binds specifically to the antigen of interest are identified, DNAs that encode the variable regions of the heavy chain and light chain of the antibody are isolated from the hybridoma cells and linked to DNAs encoding the constant regions of the heavy chain and light chain of a desired class of human antibody, respectively. The resulting gene encoding the heavy chain and light chain of the antibody is expressed in cells (e.g., CHO cells) to produce an antibody molecule. The heavy chain and light chain of the antibody produced by the above method are the heavy chain and light chain of a "fully human" antibody derived from a human immunoglobulin gene.

The anti-human CTGF antibody of the present invention can be easily prepared, based on the information on the sequence of the heavy-chain variable region and the light-chain variable region as disclosed in the present specification, using methods known in the art, by a person skilled in the art. Preferably, the anti-human CTGF antibody of the present invention can be prepared as a fully human antibody by linking the heavy-chain variable region and the light-chain variable region to a heavy-chain constant region and a light-chain constant region of a human antibody, respectively. Specifically, a heavy-chain variable region gene fragment having a base sequence encoding the heavy-chain variable region amino acid (SEQ ID NO: 10) of the antibody of the present invention and a light-chain variable region gene fragment having a base sequence encoding the light-chain variable region amino acid (SEQ ID NO: 4) of the antibody of the present invention are prepared. Further, these variable region genes are linked to a suitable class of constant region genes of a human antibody to prepare a fully human antibody gene. Subsequently, this antibody gene is linked to a suitable expression vector and introduced into cultured cells. Finally, the cultured cells are cultured and a monoclonal antibody can be obtained from the culture supernatant.

The gene fragments that encode the heavy-chain variable region and light-chain variable region amino acids of the antibody of the present invention can be synthesized using a gene synthesis method known in the art, on the basis of, for example, base sequences designed based on the amino acid sequences of the heavy chain and light chain variable regions. As such gene synthesis method, various methods known to those skilled in the art, such as the antibody gene synthesis method described in WO90/07861, can be used.

Then, the above-described variable region gene fragments are linked to the constant region genes of the human antibody to prepare a fully human antibody gene. Although any subclass of the constant region (for example, the constant region of a heavy chain such as the γ1, γ2, γ3 or γ4 chain, and the constant region of a light chain such as the λ or κ chain) can be chosen as the constant region of the human antibody used, human Igγ1 as the heavy-chain constant region, and human Igκ as the light-chain constant region, can preferably be used.

Subsequent to the preparation of this fully human antibody gene, introduction of the antibody gene into an expression vector, introduction of the expression vector into cultured cells, cultivation of the cultured cells, purification of the antibody and the like can be performed using various methods known in the art.

An expression vector that is linked to the antibody gene thus obtained includes GS vector pEE6.4 or pEE12.4 (Lonza Biologics), but are not specifically limited, so long as they can express such antibody gene. Also, an expression vector already having a human Ig constant region gene such as AG-γ1 or AG-κ (for example, see WO94/20632) may be used.

The above-described expression vector is introduced into cultured cells by, for example, a calcium phosphate method or an electroporation method and the like.

As cultured cells into which the expression vector is introduced, cultured cells such as CHO-K1SV cells, CHO-DG44 cells and 293 cells can be used, and these cells may be cultured by a conventional method.

After the above-described culture, the antibody accumulated in the culture supernatant can be purified by various column chromatography, for example, various chromatographic processes using a Protein A or Protein G column.

The anti-human CTGF antibody of the present invention is an antibody which binds to human CTGF. Examples of a method for measuring the binding activity of the obtained anti-human CTGF antibody for human CTGF include an ELISA method and a surface plasmon resonance (SPR) analysis method. For example, when ELISA is used, human CTGF (SEQ ID NO: 14) is immobilized onto an ELISA plate, and the anti-human CTGF antibody is added thereto and allowed to react therewith. Then, the resultant is allowed to react with a secondary antibody such as an anti-IgG antibody labeled with an enzyme such as horseradish peroxidase (HRP), and washed. Then, the absorbance is measured by adding a chromogenic substrate (for example, a TMB chromogenic reagent in the case of HRP labeling). Further, the binding activity for the human CTGF can be measured in more detail using SPR analysis. When SPR analysis is carried out, for example, a Biacore system can be used to measure the association rate constant (ka) and the dissociation rate constant (kd) between the anti-human CTGF antibody and the human CTGF, and thus, a dissociation constant (KD) can be calculated from the ratio of the two constants. The anti-human CTGF antibody of the present invention also includes an antibody which also binds to CTGF derived from other animals (for example, mouse CTGF), and the binding activity thereof for protein may also be measured.

Furthermore, the anti-human CTGF antibody of the present invention has neutralizing activity for human CTGF. As used in the present specification, the "neutralizing activity" of the antibody means an activity to inhibit any biological activity resulting from CTGF by the binding to CTGF, and can be evaluated on one or more biological activities of CTGF as an index. Examples of such neutralizing activity include an inhibitory action against collagen synthesis in fibroblasts derived from the kidney (inhibition of fibrosis), and the neutralizing activity can be evaluated using a method as described in Examples below.

In order to evaluate the effects of the anti-human CTGF antibody of the present invention in more detail, a test on the efficacy of the antibody in vivo can also be used. For example, by evaluating the function of the kidney using a mouse model with chronic kidney disease or a rat model with nephritis as described in Examples below, the efficacy of the antibody in vivo can be evaluated.

In addition, methods for evaluating various types of stability (for example, thermal stability, long-term storage stability and high-concentration stability) of the anti-human CTGF antibody of the present invention include differential scanning calorimetry and a method of measuring the formation of aggregates during the storage.

Preferably, the anti-human CTGF antibody of the present invention can be easily acquired by synthesizing DNA comprising a base sequence encoding the heavy-chain variable region amino acid sequence shown by SEQ ID NO: 10 and DNA comprising a base sequence encoding the light-chain variable region amino acid sequence shown by SEQ ID NO: 4, and linking these DNAs to a suitable class of human antibody constant region genes, preferably a human Igγ1 constant region gene for the heavy chain and a human Igκ constant region gene for the light chain, so as to construct a fully human antibody gene by using a method known in the art, and introducing the fully human antibody gene into an expression vector, introducing the expression vector into a cultured cell, culturing the cultured cell, and purifying an antibody from the obtained culture by using various methods known in the art. Preferably, the DNA comprising the base sequence encoding the heavy-chain variable region amino acid sequence shown by SEQ ID NO: 10 comprises the base sequence shown by SEQ ID NO: 9. Preferably, the DNA comprising the base sequence encoding the light-chain variable region amino acid sequence shown by SEQ ID NO: 4 comprises the base sequence shown by SEQ ID NO: 3.

A preferred heavy chain of anti-human CTGF antibody of the present invention, comprising the heavy-chain variable region shown by SEQ ID NO: 10 and a human Igγ1 constant region, is a heavy chain consisting of the amino acid sequence shown by SEQ ID NO: 12. A preferred light chain of anti-human CTGF antibody of the present invention, comprising the light-chain variable region shown by SEQ ID NO: 4 and a human Igκ constant region, is a light chain consisting of the amino acid sequence shown by SEQ ID NO: 8. Preferably, DNA comprising a base sequence encoding an anti-human CTGF antibody heavy chain consisting of the amino acid sequence shown by SEQ ID NO: 12 comprises the base sequence shown by SEQ ID NO: 11. Preferably, DNA comprising a base sequence encoding an anti-human CTGF antibody light chain consisting of the amino acid sequence shown by SEQ ID NO: 8 comprises the base sequence shown by SEQ ID NO: 7. An anti-human CTGF antibody of the present invention, which comprises a heavy chain consisting of the amino acid sequence shown by SEQ ID NO: 12 and a light chain consisting of the amino acid sequence shown by SEQ ID NO: 8, includes a fully human 37-45-MH1 as described in Examples below.

The present invention also comprises an anti-human CTGF antibody that comprises a heavy-chain variable region comprising CDR1 consisting of amino acid sequence at position from 31 to 35 of SEQ ID NO: 10, CDR2 consisting of amino acid sequence at position from 50 to 66 of SEQ ID NO: 10, and CDR3 consisting of amino acid sequence at position from 99 to 108 of SEQ ID NO: 10, and a light-chain variable region comprising CDR1 consisting of amino acid sequence at position from 24 to 35 of SEQ ID NO: 4, CDR2 consisting of amino acid sequence at position from 51 to 57 of SEQ ID NO: 4, and CDR3 consisting of amino acid sequence at position from 90 to 98 of SEQ ID NO: 4. The anti-human CTGF antibody can be also prepared by those skilled in the art according to procedures such as ones described above.

The present invention also comprises anti-human CTGF antibody fragments such as a single-chain variable region fragment (scFv), Fab, Fab' and F(ab')$_2$, which comprise the heavy-chain variable region and light-chain variable region of the antibody of the present invention and maintain the activity of the antibody. Any person skilled in the art can construct a fusion antibody of the anti-human CTGF antibody or antibody fragment and another peptide or protein and can also construct a modified antibody having a modifying agent bound thereto, on the basis of the present invention. The other peptide or protein used for the fusion is not specifically limited, so long as it does not reduce the binding activity of the antibody; examples thereof include human serum albumin, various tag peptides, artificial helix motif peptide, maltose-binding proteins, glutathione S transferase, various toxins, other peptides or proteins capable of promoting multimerization, and the like. The modifying agent used for the modification is not specifically limited, so long as it does not reduce the binding activity of the antibody; examples thereof include polyethylene glycol, sugar chains, phospholipids, liposomes, low-molecular compounds and the like.

The anti-human CTGF antibody of the present invention thus obtained may be further purified as necessary, and may be then formulated according to an ordinary method, and thus it can be used for prevention or treatment of diseases in which CTGF is involved in pathogenesis, such as renal diseases such as chronic kidney disease and diabetic nephropathy, vascular proliferative diseases, cardiomyopathy, hepatic fibroplasia disease, pulmonary fibrosis, skin fibrosis disease, diabetic retinopathy and cancer.

The anti-human CTGF antibody of the present invention can be preferably used as a therapeutic agent for kidney diseases, and more preferably a therapeutic agent for chronic kidney disease or diabetic nephropathy. Examples of the formulations for these therapeutic agents or the like include parenteral agents such as an injection agent and an infusion agent, and administration thereof using intravenous administration, subcutaneous administration, or the like is preferred. In addition, for the formulation, within a pharmaceutically acceptable range, a carrier or an additive can be used according to these formulations.

The amount of the anti-human CTGF antibody of the present invention added in the above-described formulation varies depending on the patient's symptom severity or age, the dosage form of the formulation used or the binding titer of the antibody and the like; for example, about 0.001 mg/kg to 100 mg/kg of the antibody may be used.

The present invention also provides a polynucleotide comprising a sequence encoding an anti-human CTGF antibody of the present invention, and an expression vector comprising the same. The present invention also provides a polynucleotide comprising a sequence encoding the heavy-chain variable region of the anti-human CTGF antibody of the present invention, and a polynucleotide comprising a sequence encoding the light-chain variable region of the anti-human CTGF antibody of the present invention, and expression vector comprising either or both of them. The expression vector of the present invention is not specifically limited, so long as it can express a gene that encodes the antibody of the present invention or its heavy-chain variable region and/or light-chain variable region in various host cells of prokaryotic cells and/or eukaryotic cells, and produce these polypeptides. Examples thereof include plasmid vectors, viral vectors (for example, adenovirus, retrovirus) and the like. Preferably, the expression vector of the present invention comprises a polynucleotide comprising either a sequence encoding the heavy chain or light chain of the above-described antibody of the present invention, or both a polynucleotide comprising a sequence encoding the heavy chain of the antibody of the present invention and a polynucleotide comprising a sequence encoding the light chain of the antibody of the present invention.

The expression vector of the present invention can comprise a promoter operably linked to a gene that encodes the anti-human CTGF antibody of the present invention or its heavy-chain variable region and/or light-chain variable region. A promoter for expressing a gene encoding the antibody of the present invention or its heavy-chain variable region and/or light-chain variable region in a bacterium includes, for example, Trp promoter, lac promoter, recA promoter, λPL promoter, lpp promoter, tac promoter and the like, when the host is a bacterium of the genus *Escherichia*. A promoter for expression in yeast includes, for example, PH05 promoter, PGK promoter, GAP promoter and ADH promoter, and some examples of a promoter for expression in the genus *Bacillus* include SL01 promoter, SP02 promoter, penP promoter and the like. When the host is a eukaryotic cell such as a mammalian cell, a promoter includes SV40-derived promoter, retrovirus promoter, heat shock promoter and the like.

When a bacterium, particularly *Escherichia coli*, is used as the host cell, the expression vector of the present invention can further comprise an initiation codon, a stop codon, a terminator region and a replicable unit. When yeast, an animal cell or insect cell is used as the host, the expression vector of the present invention can comprise an initiation codon and a stop codon. In this case, it may comprise an enhancer sequence, noncoding regions on the 5' side and 3' side of a gene that encodes the antibody of the present invention or its heavy-chain variable region or light-chain variable region, a secretion signal sequence, a splicing junction, a polyadenylation region, a replicable unit or the like. Also, it may comprise a selection marker that is in common use (for example, tetracycline-resistant gene, ampicillin-resistant gene, kanamycin-resistant gene, neomycin-resistant gene, dihydrofolic acid reductase gene) according to the intended use.

The present invention also provides a transformant introduced with a gene encoding the antibody of the present invention or its heavy-chain variable region and/or light-chain variable region. Such a transformant can be prepared by, for example, transforming a host cell with the expression vector of the present invention. A host cell that is used to prepare the transformant is not specifically limited, so long as it is suitable for the aforementioned expression vector and is transformable; examples thereof include various cells such as natural cells or artificially established cells commonly being used in the technical field of the present invention (for example, bacteria (bacteria of the genus *Escherichia*, bacteria of the genus *Bacillus*), yeasts (the genus *Saccharomyces*, the genus *Pichia* and the like), animal cells or insect cells (for example, Sf9) and the like. The transformation can be performed by any known method per se.

Preferably, the transformant of the present invention is a host cell transformed with an expression vector comprising a polynucleotide comprising a sequence encoding the heavy-chain variable region of the antibody of the present invention and a polynucleotide comprising a sequence encoding the light-chain variable region of the antibody of the present invention, or a host cell transformed with an expression vector comprising a polynucleotide comprising a sequence encoding the heavy-chain variable region of the antibody of the present invention and an expression vector comprising a polynucleotide comprising a sequence encoding the light-chain variable region of the antibody of the present invention. More preferably, the transformant of the present invention is a host cell transformed with an expression vector comprising a polynucleotide comprising a sequence encoding the heavy chain of the antibody of the present invention as described above and a polynucleotide comprising a sequence encoding the light chain of the antibody of the present invention, or a host cell transformed with an expression vector comprising a polynucleotide comprising a sequence encoding the heavy chain of the antibody of the present invention as described above and an expression vector comprising a polynucleotide comprising a sequence encoding the light chain of the antibody of the present invention.

The present invention further provides a method for producing the anti-human CTGF antibody of the present invention, comprising expressing a gene encoding the antibody of the present invention or the heavy-chain variable region and/or the light-chain variable region thereof in a host cell, that is, using such a transformant. Preferably, the host cell used in the method is a host cell transformed with the expression vector of the present invention as described above, and the expression vector may comprise a polynucleotide comprising a sequence encoding the heavy-chain variable region of the antibody of the present invention and a polynucleotide comprising a sequence encoding the light-chain variable region of the antibody of the present invention, separately or simultaneously.

When producing the anti-human CTGF antibody of the present invention, the transformant may be cultured in a nutrient medium. The nutrient medium preferably contains a carbon source and an inorganic nitrogen source or organic nitrogen source, which are required for the growth of the transformant. Examples of the carbon source include glucose, dextran, soluble starch, sucrose and the like; examples of the inorganic nitrogen source or organic nitrogen source include ammonium salts, nitrates, amino acids, corn steep liquor, peptone, casein, meat extract, soybean cake, potato extract and the like. If desired, other nutrients (for example, inorganic salts (for example, calcium chloride, sodium dihydrogen phosphate, magnesium chloride), vitamins, antibiotics (for example, tetracycline, neomycin, ampicillin, kanamycin and the like) and the like) may be contained.

Culture of the transformant is performed by a method known per se. Culture conditions, for example, temperature, pH of the medium, and culture time are suitably selected. For example, when the host is an animal cell, an MEM medium (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) and the like containing about 5% to 20% fetal bovine serum can be used as the medium. The pH of the medium is preferably about 6 to 8, culture is normally performed at about 30° C. to 40° C. for about 15 to 72 hours, and aeration or agitation may be performed as necessary. When the host is an insect cell, for example, Grace's medium (Proc. Natl. Acad. Sci. USA, Vol. 82, p. 8404, 1985) and the like containing fetal bovine serum can be mentioned, and the pH thereof is preferably about 5 to 8. Culturing is normally performed at about 20° C. to 40° C. for 15 to 100 hours, and aeration or agitation may be performed as necessary. When the host is a bacterium, an actinomyces, yeast, or a filamentous fungus, for example, a liquid medium containing the above-described nutrient sources is appropriate. A medium having a pH of 5 to 8 is preferable. When the host is *E. coli*, preferred examples of the medium include LB medium, M9 medium (Miller et al., Exp. Mol. Genet, Cold Spring Harbor Laboratory, p. 431, 1972) and the like. In this case, culture can be normally performed at 14° C. to 43° C. for about 3 to 24 hours, while aeration or agitation is performed as necessary. When the host is a bacterium of the genus *Bacillus*, cultivation can be normally performed at 30° C. to 40° C. for about 16 to 96 hours, while aeration or agitation is performed as necessary. When the host is yeast, examples of the medium include Burkholder's minimal medium (Bostian, Proc. Natl. Acad. Sci. USA, Vol. 77, p. 4505, 1980), and the pH of the medium is desirably 5 to 8. Culturing is normally performed at about 20° C. to 35° C. for about 14 to 144 hours, and aeration or agitation may be performed as necessary.

By culturing a transformant as described above, the anti-human CTGF antibody of the present invention can be recovered, preferably isolated and purified, from the transformant. Examples of the method of isolation and purification include methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing; and the like.

Although the present invention has been generally described above, specific examples are provided herein only for a better understanding of the present invention. These examples are for illustrative purposes only and do not limit the scope of the present invention.

EXAMPLES

The procedures involving the use of a kit or a reagent and the like were performed in accordance with the attached protocol attached unless otherwise stated.

Example 1

Acquisition of CTGF Protein Derived from Various Sources

The present inventors acquired a human CTGF protein as an antigen for preparing an anti-CTGF antibody. The full-length gene (SEQ ID NO: 13) of the human CTGF was ligated into an expression vector (pcDNA3.1; Invitrogen), and the vector thus prepared was genetically introduced into a FreeStyle 293 cell (Invitrogen) using a FreeStyle MAX Reagent (Invitrogen) as a gene introducing reagent. This cell was cultured in a serum-free culture system using a FreeStyle 293 Expression Medium (Invitrogen), and then a culture supernatant including the human CTGF protein was acquired. Protein was purified from the culture supernatant thus acquired, using a HiTrap heparin column and a CM column (GE Healthcare Japan), and then used in the experiment as follows. Mouse, rat and monkey CTGF proteins were acquired using the same method.

Example 2

Immunization of VelocImmune Mouse

An antibody for human CTGF was acquired by immunization for a VelocImmune mouse. In order to increase the diversity of an antibody to be obtained, the present inventors have investigated a plurality of immunization methods, administration routes, adjuvants, immune periods, and the like. As an immunogen, purified human CTGF was used and mixed with an adjuvant to perform immunization. As the administration route, footpad administration and intraperitoneal administration were investigated. As the adjuvant, TiterMax Gold (CytRx Corporation), a complete Freund's adjuvant (Sigma), and an incomplete Freund's adjuvant (Sigma) were investigated. In addition, as an immunestimulant to be added, CpG oligonucleotide and Aluminum Phosphate Gel (manufactured by BRENNTAG) were investigated. As for the immunization period, the immunization was performed for 3 weeks to 14 weeks. After performing immunization several times, mice were subjected to blood sampling from caudal vein to monitor a titer, and thus, VelocImmune mice that produce antibodies binding to human CTGF were chosen.

The titration was measured using a standard ELISA method below. 20 µL of phosphate buffer physiological saline (PBS) solution of human CTGF (1 µg/mL) was added to a Maxisorp 384 plate (Nunc, Inc.), and immobilized by being incubated overnight at 4° C. The next day, the plate was washed once with 100 µL of washing solution (TBST:

0.05% Tween-20-containing Tris buffer), and then 100 µL of blocking agent (1% BSA-containing PBS) was added thereto and allowed to stand at room temperature for 1 hour. After washing once with 100 µL of TBST washing solution, a series of dilutions of plasma in the sampled blood were prepared and added thereto. After incubation at room temperature for 1 hour, and washing with 100 µL of TBST washing solution three times, a goat anti-mouse IgG antibody labeled with a horseradish peroxidase (HRP-goat anti-mouse IgG antibody; Zymed Laboratories, Inc.) that had been diluted 5000-fold with a 0.1% BSA-containing TBST washing solution (20 µL) was added thereto. After incubation at room temperature for 1 hour, washing with 100 µL of TBST washing solution was conducted three times. After adding 40 µL of TMB chromogenic reagent (Sumitomo Bakelite Co., Ltd.) thereto and allowing it to stand at room temperature for 10 minutes, 40 µL of stopping solution (2 mol/L sulfuric acid) was added thereto to stop the reaction, and the absorbance at 450 nm was measured.

Example 3

Preparation of Anti-Human CTGF Antibody-Producing Hybridoma

Final immunization (intravenous administration or intraperitoneal administration of an antigen) was carried out for a mouse chosen by checking the increase in the antibody titer. A hybridoma was prepared by collecting lymphocytes by removing spleen and lymph nodes of immunized mice according to a conventional method, and cell-fusing them into a mouse myeloma cell SP2/0. The hybridoma was subjected to limiting dilution and monocloning, and then the antibody was purified from the supernatant using a protein A or protein G column (GE Healthcare Japan).

Example 4

ELISA Assay

The present inventors evaluated the binding specificity of the antibody for CTGF using an ELISA method. 20 µL of PBS solution of human CTGF (1 µg/mL) was added to a Maxisorp 384 plate (Nunc, Inc.), and immobilized by being incubated overnight at 4° C. The next day, the plate was washed once with 100 µL of washing solution (TPBS: 0.05% Tween-20-containing PBS), and then 100 µL of blocking agent (1% BSA-containing PBS) was added thereto and allowed to stand at room temperature for 1 hour. After washing once with 100 µL of TBST washing solution, a series of appropriate dilutions of the purified antibody sample were prepared and added to the plate. After incubation at room temperature for 1 hour, the plate was washed three times with 100 µL of TBST washing solution, and a goat anti-mouse IgG antibody labeled with a horseradish peroxidase (HRP-goat anti-mouse IgG antibody; Zymed Laboratories, Inc.) which was diluted 5000-fold with a 0.1% BSA-containing TBST washing solution (20 µL) was added thereto. After incubation at room temperature for 1 hour, the plate was washed three times with 100 µL of TBST washing solution. After adding 40 µL of TMB chromogenic reagent (Sumitomo Bakelite Co., Ltd.) thereto and allowing it to stand at room temperature for 10 minutes, 40 µL of stopping solution (2 mol/L sulfuric acid) was added thereto to stop the reaction, and the absorbance at 450 nm was measured. Each of the antibodies was tested in duplicate, and the EC50 was analyzed by curve fitting.

As a result, it was confirmed that an antibody referred to as 37-45 has high binding activity (EC50: 1.6 ng/ml).

Example 5

Sequencing of Antibody

For the identified 37-45 antibody, the present inventors cloned a gene encoding the heavy chain and light chain of the antibody from the hybridoma. RNA was extracted from the hybridoma, and a cDNA was prepared using a cDNA amplification kit (SMARTer RACE cDNA Amplification kit; Clontech). Subsequently, the variable regions of the heavy chain and light chain were elongated and amplified using PCR. The PCR products were recombined with a vector for subcloning PCR products such as pCR3.1-TOPO (Invitrogen), and then the gene was sequenced using a sequencer (ABI PRISM 3100; Applied Biosystems).

The determined base sequence of the heavy-chain variable region of 37-45 is shown by SEQ ID NO: 1 and the amino acid sequence thereof is shown by SEQ ID NO: 2, and the determined base sequence of the light-chain variable region of 37-45 is shown by SEQ ID NO: 3 and the amino acid sequence thereof is shown by SEQ ID NO: 4.

Example 6

Preparation of Fully Human Antibody

For the above-described antibody, the variable region is derived from a human and the constant region is derived from a mouse. Therefore, the present inventors replaced the constant region derived from a mouse by the constant region derived from a human to prepare a fully human antibody (fully human 37-45). Specifically, a signal sequence was linked to the 5' side of the heavy-chain variable region gene of the antibody and the constant region gene of human Igγ1 (Man Sung Co., etc. (1992) J Immunol. Vol. 148 (4): 1149-1154) was linked to the 3' side of the heavy-chain variable region gene of the antibody. The heavy-chain gene was inserted into a GS vector (Lonza Biologics) pEE6.4. Upon insertion, a restriction enzyme BbvCI recognizing site in the gene was converted to a DNA sequence that does not affect the amino acid sequence of the antibody. In addition, a signal sequence was linked to the 5' side of the light-chain variable region gene of the antibody and the constant region gene of human κ chain (Man Sung Co., etc., supra) was linked to the 3' side of the light-chain variable region gene of the antibody. The light-chain gene was inserted into a GS vector pEE12.4.

For the heavy chain of the prepared fully human 37-45, the base sequence is shown by SEQ ID NO: 5 and the amino acid sequence is shown by SEQ ID NO: 6, and for the light chain of the antibody, the base sequence is shown by as SEQ ID NO: 7 and the amino acid sequence is shown by SEQ ID NO: 8.

Example 7

Preparation of Variant of Glycosylation Site of Variable Region

The amino acid of the heavy-chain variable region of fully human 37-45 as described above includes an N-type glycosylation motif sequence of N-X-(T/S). Specifically, in the heavy-chain variable region shown by SEQ ID NO: 2, Asn at the position 58 according to Kabat numbering corresponds to the glycosylation site. If the glycosylation site is present, addition of sugar chains to the antibody occurs during cell culture, but it is known that the addition of sugar chains depends on culture conditions or hosts for expression. That is, even with the same antibody-producing cells thus established, there is a possibility that a degree of the addition of sugar chains varies according to culture conditions (a medium, a cell concentration, and the like), and there is also a possibility that it is difficult to acquire an antibody medical product having uniform quality. Therefore, the present inventors prepared a fully human antibody (fully human 37-45-MH1) in which mutations had been introduced to the heavy-chain variable region of fully human 37-45.

For the heavy-chain variable region of the prepared fully human 37-45-MH1, the base sequence is shown by SEQ ID NO: 9 and the amino acid sequence is shown by SEQ ID NO: 10. For the heavy chain of the prepared fully human 37-45-MH1, the base sequence is shown by SEQ ID NO: 11 and the amino acid sequence is shown by SEQ ID NO: 12. The light chain of fully human 37-45-MH1 is the same as the light chain of fully human 37-45.

The CDR1, CDR2 and CDR3 of the heavy-chain variable region of fully human 37-45-MH1 antibody is a region of position from 31 to 35, 50 to 65, and 95 to 102 of the heavy-chain variable region based on Kabat numbering, respectively, which consists of the amino acid sequence at position from 31 to 35, 50 to 66, and 99 to 108 of SEQ ID NO:10, respectively. The CDR1, CDR2 and CDR3 of the light-chain variable region of fully human 37-45-MH1 antibody is a region of position from 24 to 34, 50 to 56, and 89 to 97 of the light-chain variable region based on Kabat numbering, respectively, which consists of the amino acid sequence at position from 24 to 35, 51 to 57, and 90 to 98 of SEQ ID NO:4, respectively.

Example 8

Expression and Purification of Fully Human Antibody

The GS vector in which the genes of the heavy chain and light chain of each antibody as described above, fully human 37-45 and fully human 37-45-MH1, has been inserted was cleaved with restriction enzymes, NotI and PvuI, and ligated using a Ligation-Convenience Kit (NIPPONGENE) or a Ligation-high (TOYOBO) to construct a GS vector in which both genes of the heavy chain and light chain had been inserted. This vector encodes the full-length heavy and light chains, and a glutamine synthetase, and it was transfected into CHO-K1SV cells to express an antibody. The culture supernatant was purified with a Protein A or Protein G column (GE Healthcare Japan) to obtain a purified antibody of each fully human antibody.

Example 9

ELISA Assay of Fully Human Antibody

The present inventors evaluated the binding specificity of fully human 37-45 and fully human 37-45-MH1 prepared in the above Examples to human, mouse, rat and monkey CTGF using an ELISA method. Here, the same method as described in Example 4 was used, but a rabbit anti-human IgG antibody labeled with horseradish peroxidase (HRP-rabbit anti-human IgG antibody; DAKO) which was 5000-fold diluted with a 0.1% BSA-containing TBST washing solution as a secondary antibody. The test on each antibody was carried out in duplicate and EC50 was analyzed by curve fitting.

As a result, it was found that all of fully human antibodies had the same degrees of binding ability for human, mouse, rat and monkey CTGF.

TABLE 1

Binding Activity of Fully Human Antibody for Various CTGF

| | Fully human 37-45 EC50 (ng/ml) | Fully human 37-45-MH1 EC50 (ng/ml) |
|---|---|---|
| Human CTGF | 13.2 | 10.4 |
| Mouse CTGF | 12.4 | 9.2 |
| Rat CTGF | 13.1 | 9.2 |
| Monkey CTGF | 12.5 | 8.6 |

Example 10

Evaluation of Binding Activity by SPR Analysis

In order to measure the antigen-specific binding activity of fully human 37-45-MH1 in more detail, the present inventors carried out surface plasmon resonance (SPR) analysis. In the present Example, an anti-human CTGF antibody CLN1 (Patent Document 2) was used as a comparative antibody.

In the SPR analysis, Biacore 2000 (GE Healthcare Japan) was used to carry out analysis. An anti-CTGF antibody was immobilized on the surface of a Sensor Chip CM5 using a Human Antibody Capture Kit and an Amine Coupling Kit (GE Healthcare Japan). Serial dilution of the human CTGF acquired in Example 1 was made by HBS-EP solution (GE Healthcare Japan). 100 μL of the dilution was added to flow path at flow rate 50 μl/min. By this measurement system, the association rate constant (ka), the dissociation rate constant (kd), and the dissociation constant (KD) between the human CTGF protein and the anti-CTGF antibody were calculated using a data analysis software (BIA Evaluation).

TABLE 2

Binding Activity to human CTGF of Fully Human 37-45-MH1 by SPR Analysis

| | KD (M) | Kd (1/s) |
|---|---|---|
| Fully human 37-45-MH1 | $3.7 \times 10^{-11}$ | $1.6 \times 10^{-4}$ |
| CLN1 | $4.6 \times 10^{-10}$ | $3.7 \times 10^{-3}$ |

As a result, it was found that fully human 37-45-MH1 has about 12 times or higher binding activity for human CTGF than that of the antibody CLN1.

Example 11

Inhibitory Action on Collagen Synthesis in Rat Kidney-Derived Cells

The present inventors investigated the inhibitory effect on TGFβ-induced collagen synthesis in the rat fibroblast NRK-49F in order to measure the antigen-specific neutralizing action of fully human 37-45-MH1. In the present Example, CLN1 was used as a comparative antibody.

NRK-49F cells (available from ATCC) produce CTGF by the addition of TGFβ. The NRK-49F cells were seeded into a 24-well plate in a 10% FCS-containing DMEM medium ($5\times10^4$ cells), and after 24 hours, the medium was replaced with a 0.01% FCS-containing DMEM (500 μL). Further, after 24 hours, TGFβ (R&D Systems; 1 ng/ml) was added to the medium. At 1 hour before the addition of TGFβ, anti-human CTGF antibodies, fully human 37-45-MH1 or CLN1, were added (to three groups at 1 μg/ml, 3 μg/ml and 10 μg/ml). After 72 hours, the supernatant was recovered and subjected to SDS-PAGE, and Western Blot analysis was carried out according to an ordinary method using an Anti-Collagen I antibody (Abcam plc). As a result, it was found that fully human 37-45-MH1 has a strong ability of inhibiting collagen synthesis, as compared with CLN1 in a concentration-dependent manner.

Example 12

Evaluation Test on Kidney Function by Mouse Remnant Kidney Model

Glomerulosclerosis and renal tubular degeneration are a finding, which appears commonly in a variety of renal disorders causing chronic renal diseases. These chronic renal diseases can be investigated in the mouse remnant kidney model exhibiting progressive renal disorders. In this model, a load is applied to the residual kidney by ⅔ unilateral nephrectomy and contralateral total nephrectomy (5/6 nephrectomy), thereby inducing proteinuria and significant reduction in the functions of the kidney, and histopathological glomerular sclerosis or renal tubular degeneration is shown and mild interstitial fibrosis is shown (see, for example, Kidney International, 64, 350-355, 2003).

5/6 Nephrectomy was carried out with reference to a method of Zhang, et al. (Kidney International, 56, 549-558, 1999). A 9-week-old male mouse ICR (Japan SLC, Inc., Hamamatsu-shi, Shizuoka-ken) was anesthetized by the intraperitoneal administration of pentobarbital (50 mg/kg), and the head ⅓ and the caudal ⅓ of the left kidney were resected. One week after the first surgery, the mouse was anesthetized by intraperitoneal administration of pentobarbital (50 mg/kg), and the right kidney was completely removed to complete the 5/6 nephrectomy.

Urine collection and blood sampling were performed one week after the 5/6 nephrectomy, and urinary protein excretion rate and renal function parameters (serum creatinine concentration and creatinine clearance) were measured. The protein concentration measurement was performed by a Bradford method (Bio-Rad Laboratories). The creatinine concentration was measured using CRE-EN Kainos (Kainos Laboratories, Inc.). The urinary protein excretion rate was calculated by correcting the urinary protein concentration (mg/ml) with the urinary creatinine concentration (mg/dL). The urinary protein excretion rate, the serum creatinine concentration, and the creatinine clearance were taken as indicators, and thus, the groups were divided into solvent-treated group (administration of a phosphate buffer with pH 7.4) and antibody administration group (15 mice per group). The tests started by setting the doses of antibodies to three groups, 0.5 mg/kg, 1 mg/kg and 2 mg/kg. The phosphate buffer and fully human 37-45-MH1 were injected subcutaneously into the back once a week (six doses in total). At the start of the test, at weeks 4 and 6 from the start of the test, the urine samples and the blood samples were collected, and the urinary protein excretion rate, the serum creatinine concentration, and the creatinine clearance were measured.

For the urinary protein excretion rate, at a time of the start of the test, in the solvent-treated group, the urinary protein excretion rate increased, as compared with the normal group (normal group 5.1±0.4; solvent-treated group 9.7±0.7 (P<0.01)). Also, at weeks 4 and 6 from the start of the test, in the solvent-treated group, the urinary protein excretion rate increased, as compared with the normal group. On the other hand, in the antibody-treated groups (1 mg/kg group and 2 mg/kg group), although there was no statistically significant difference, the urinary protein excretion rate decreased in a dose-dependent manner, as compared with the solvent-treated group.

For the serum creatinine concentration, at a time of the start of the test, in the solvent-treated group, the serum creatinine concentration increased, as compared with the normal group (normal group 0.36±0.013 mg/dL; solvent-treated group 0.53±0.016 mg/dL (P<0.01)). Thereafter, also at weeks 4 and 6, in the solvent-treated group, the serum creatinine concentration increased, as compared with the normal group (week 4: normal group 0.42±0.025 mg/dL; solvent-treated group 0.66±0.037 mg/dL (P<0.01), week 6: normal group 0.31±0.016 mg/dL; solvent-treated group 0.81±0.126 mg/dL (P<0.05)). In the antibody-treated groups, for the 0.5 mg/kg group, although there was no significant difference, the serum creatinine concentration decreased at weeks 4 and 6, as compared with the solvent-treated group. In addition, in the 1 mg/kg group and the 2 mg/kg group, the increase in the serum creatinine concentration was significantly inhibited, as compared with the solvent-treated group (week 4: 1 mg/kg group 0.51±0.022 mg/dL (P<0.05); 2 mg/kg group 0.51±0.015 mg/dL (P<0.05), week 6: 1 mg/kg group 0.55±0.043 mg/dL (P<0.05); 2 mg/kg group 0.49±0.024 mg/dL (P<0.01)).

For the creatinine clearance (urinary creatinine concentration×amount of urine for 24 hours/serum creatinine concentration), at a time of the start of the test, in the solvent-treated group, the decrease in the creatinine clearance was confirmed as compared with the normal group (normal group 1.8±0.18; solvent-treated group 1.3±0.08 (P<0.01)). Thereafter, also at weeks 4 and 6, in the solvent-treated group, the creatinine clearance decreased as compared with the normal group (week 4: normal group 2.1±0.16; solvent-treated group 1.6±0.16, week 6: normal group 2.8±0.29; solvent-treated group 1.4±0.17 (P<0.001)). For the antibody-treated groups, in the 0.5 mg/kg group, inhibition of the decrease in the creatinine clearance was not confirmed as compared with the solvent-treated group. On the other hand, in the 1 mg/kg group, at weeks 4 and 6, the decrease in the creatinine clearance was significantly inhibited, as compared with the solvent-treated group (week 4: solvent-treated group 1.6±0.16; 1 mg/kg group 2.1±0.11 (P<0.05), week 6: solvent-treated group 1.4±0.17; 1 mg/kg group 2.0±0.18 (P<0.05)). In addition, in the 2 mg/kg group, at week 6, the decrease in the creatinine clearance was significantly inhibited, as compared with the solvent-treated group (week 6: solvent-treated group 1.4±0.17; 2 mg/kg group 1.9±0.14 (P<0.05)).

From these results, it was confirmed that fully human 37-45-MH1 inhibits reduction in the renal functions in a chronic kidney disease model.

Example 13

Pharmacological Evaluation Test on Rat Nephritis Models

Rat anti-Thy 1.1 models are established mesangial proliferative glomerulonephritis models, with the pathological conditions expressed by the injection of antibodies to Thy antigens on the surface of mesangial cells in the renal glomeruli (see, for example, Yamamoto and Wilson, 1987 Kidney Int. 32:514-25, Morita, et al., 1998 Am J Kidney Dis 31:559-73). In the present models, after the lysis of the mesangial cells, mesangial cell proliferation and extracellular matrices increase, and the level of urine protein is enhanced (see, for example, Floege, et al., 1991 Kidney Int. 40:477-88, Ito, et al., 2001 J Am Soc Nephrol. 12:472-84). The anti-Thy 1.1 models are similar to IgA nephropathy or Henoch-Schonlein purpura in human, and the progress of the pathological conditions can be predicted using the models with proteinuria as an indicator (see, for example, Kasuga, et al., 2001 Kidney Int. 60:1745-55, Liu, et al., 2007 Nephron Exp Nephrol. 105:e65-74).

A solution of anti-Thy 1.1 antibody (Anti-Rat CD90 (Thy 1.1) monoclonal antibody-ascites; CEDARLANE) was prepared by physiological saline at 0.1 g/mL. Nephritis was expressed by intravenously administering the antibody solution to rats (200 μL per 100 g body weight). After 4 hours from the administration of anti-Thy 1.1 antibodies, fully human 37-45-MH1 (0.5 mg/kg, 1 mg/kg or 2 mg/kg) or solvent (PBS) were intravenously administered. Urine collection were performed for 24 hours after 3 to 4 days from the induction of the pathogenesis, and the urinary protein excretion amount in 24 hours (UP) and the urinary protein excretion rate (UP/uCr: the urinary protein concentration (mg/ml) was corrected with the urinary creatinine concentration (mg/dL)) were measured. The results are shown in Table 3 (UP) and Table 4 (UP/uCr).

TABLE 3

| | UP | UP (mg/day) | Inhibitory rate (%) vs solvent-administered group | p value |
|---|---|---|---|---|
| Normal animal group | | 1.9 | 100.0 | |
| Solvent-administered group (PBS) | | 114.3 | 0.0 | p < 0.001 # |
| Fully human 37-45-MH1 0.5 mg/kg | | 115.2 | −0.8 | |
| Fully human 37-45-MH1 1 mg/kg | | 95.5 | 16.8 | |
| Fully human 37-45-MH1 2 mg/kg | | 83.8 | 27.2 | p = 0.029 * |

: vs normal animal group by t-test
*: vs solvent-administered group by Dunnett's test

TABLE 4

| | UP/uCr | | |
|---|---|---|---|
| | UP/uCr (mg/mg) | Inhibitory rate (%) vs solvent-administered group | p value |
| Normal animal group | 0.315 | 100.0 | |
| Solvent-administered group (PBS) | 33.865 | 0.0 | p < 0.001 # |
| Fully human 37-45-MH1 0.5 mg/kg | 26.280 | 22.6 | |
| Fully human 37-45-MH1 1 mg/kg | 22.487 | 33.9 | p = 0.037 * |
| Fully human 37-45-MH1 2 mg/kg | 18.427 | 46.0 | p = 0.0039 * |

: vs normal animal group by t-test
*: vs solvent-administered group by Dunnett's test As a result, fully human 37-45-MH1 inhibited the proteinuria in a dose-dependent manner, and the inhibitory rates at 2 mg/kg group were 27.2% and 46.0% vs solvent-administered group, respectively, with the indices of UP and UP/uCr.

Next, for the purpose of identifying the difference from CLN1 in the action strength, the same models were used for evaluation. The evaluation procedure was the same as above. For the evaluation, with reference to the doses which were effective in the above, 2 mg/kg of fully human 37-45-MH1 was used as a positive control, and 2 mg/kg and a 10-times dose thereof, 20 mg/kg, of CLN1 were used. Further, for the purpose of investigating the involvement of a non-specific immune reaction by the treatment with heterogenetic antibodies, 2 mg/kg and 20 mg/kg of human IgG1 antibodies (anti-KLH (keyhole limpet hemocyanin) antibody: it was obtained by immunizing a VelocImmune mouse with KLH and preparing as a fully human IgG1 in the same way of the fully human 37-45-MH1) were used as controls. The results are shown in Table 5 (UP) and Table 6 (UP/uCr).

TABLE 5

| | UP | | | | |
|---|---|---|---|---|---|
| | UP (mg/day) | Inhibitory rate (%) vs solvent-administered group | p value | Inhibitory rate (%) vs IgG-administered group | p value |
| Normal animal group | 0.8 | 100.0 | | 100.0 | |
| Solvent-administered group (PBS) | 111.1 | 0.0 | p < 0.001 # | | |
| Control IgG 2 mg/kg | 114.5 | −3.1 | | 0.0 | p < 0.001 # |
| Control IgG 20 mg/kg | 113.4 | −2.1 | | 0.0 | p < 0.001 # |
| CLN1 2 mg/kg | 97.2 | 12.6 | p = 0.45 * | 15.2 | p = 0.22 & |
| CLN1 20 mg/kg | 107.3 | 3.5 | p = 0.79 * | 5.4 | p = 0.53 $ |

TABLE 5-continued

| | UP | | | | |
|---|---|---|---|---|---|
| | UP (mg/day) | Inhibitory rate (%) vs solvent-administered group | p value | Inhibitory rate (%) vs IgG-administered group | p value |
| Fully human 37-45-MH1 2 mg/kg | 79.0 | 29.1 | p = 0.044 * | 31.2 | p = 0.0011 & |

\#: vs normal animal group by t-test
*: vs solvent-administered group by t-test
&: vs Control IgG 2 mg/kg group by t-test
$: vs Control IgG 20 mg/kg group by t-test

TABLE 6

| | UP/uCr | | | | |
|---|---|---|---|---|---|
| | UP/uCr (mg/mg) | Inhibitory rate (%) vs solvent-administered group | p value | Inhibitory rate (%) vs IgG-administered group | p value |
| Normal animal group | 0.3 | 100.0 | | 100.0 | |
| Solvent-administered group (PBS) | 46.1 | 0.0 | p < 0.001 # | | |
| Control IgG 2 mg/kg | 52.2 | −13.4 | | 0.0 | p < 0.001 # |
| Control IgG 20 mg/kg | 42.7 | 7.5 | | 0.0 | p < 0.001 # |
| CLN1 2 mg/kg | 36.3 | 21.5 | p = 0.18 * | 30.8 | p = 0.030 & |
| CLN1 20 mg/kg | 41.8 | 9.5 | p = 0.49 * | 2.2 | p = 0.82 $ |
| Fully human 37-45-MH1 2 mg/kg | 28.1 | 39.2 | p = 0.0092 * | 46.4 | p < 0.001 & |

\#: vs normal animal group by t-test
*: vs solvent-administered group by t-test
&: vs Control IgG 2 mg/kg group by t-test
$: vs Control IgG 20 mg/kg group by t-test As a result, the pathological conditions were expressed in substantially the same degree as the previous experiment. In addition, 2 mg/kg of fully human 37-45-MH1 showed substantially the same inhibitory rate as evaluated in the previous experiment, and the inhibitory rates were 29.1% and 39.2%, respectively, with the indices of UP and UP/uCr, in the case of using the solvent-administered group as a control.

On the other hand, CLN1 had a less inhibitory action on proteinuria, as compared with the fully human 37-45-MH1 (the inhibitory rates vs solvent-administered group were 12.6% and 21.5%, respectively, with the indices of UP and UP/uCr at 2 mg/kg, and the inhibitory rates vs solvent-administered group were 3.5% and 9.5%, respectively, with the indices of UP and UP/uCr at 20 mg/kg). Further, for the human IgG1 antibodies, there was a substantially little action on proteinuria.

From this, it was confirmed that fully human 37-45-MH1 has a strong proteinuria inhibitory action, as compared with CLN1.

INDUSTRIAL APPLICABILITY

The anti-human CTGF antibody of the present invention is useful for prevention or treatment of various diseases that human CTGF is involved in pathogenesis, in a range of renal diseases such as chronic kidney disease and diabetic nephropathy.

The invention claimed is:

1. An anti-human CTGF antibody or anti-human CTGF antibody fragment, comprising:
    a heavy-chain variable region consisting of the amino acid sequence shown by SEQ ID NO: 10; and
    a light-chain variable region consisting of the amino acid sequence shown by SEQ ID NO: 4.

2. The anti-human CTGF antibody or anti-human CTGF antibody fragment according to claim 1, comprising a heavy chain constant region which is a human Igγ1 constant region.

3. The anti-human CTGF antibody or anti-human CTGF antibody fragment according to claim 1, comprising a light chain constant region which is a human Igκ constant region.

4. The anti-human CTGF antibody or anti-human CTGF antibody fragment according to claim 1, comprising a heavy chain constant region which is a human Igγ1 constant region and a light chain constant region which is a human Igκ constant region.

5. The anti-human CTGF antibody according to claim 1, comprising:
    a heavy chain consisting of the amino acid sequence shown by SEQ ID NO: 12; and
    a light chain consisting of the amino acid sequence shown by SEQ ID NO: 8.

6. A polynucleotide comprising a sequence that encodes the heavy-chain variable region of the antibody or antibody fragment according to claim 1.

7. An expression vector comprising the polynucleotide according to claim 6.

8. A host cell transformed with the expression vector according to claim 7.

9. A polynucleotide comprising a sequence that encodes the light-chain variable region of the antibody or antibody fragment according to claim 1.

10. An expression vector comprising the polynucleotide according to claim 9.

11. A host cell transformed with the expression vector according to claim 10.

12. The anti-human CTGF antibody fragment according to claim 1, wherein the fragment is a single-chain variable region fragment, Fab, Fab', or F(ab')₂.

13. The anti-human CTGF antibody or anti-human CTGF antibody fragment according to claim 1, wherein the antibody or the fragment is fused with another peptide or protein, or is modified with polyethylene glycol.

14. A host cell, which is selected from the group consisting of:
    a host cell transformed with an expression vector comprising a polynucleotide comprising a sequence that encodes a heavy-chain variable region consisting of the amino acid sequence shown by SEQ ID NO: 10 and a polynucleotide comprising a sequence that encodes a light-chain variable region consisting of the amino acid sequence shown by SEQ ID NO: 4; and
    a host cell transformed with an expression vector comprising a polynucleotide comprising a sequence that encodes a heavy-chain variable region consisting of the amino acid sequence shown by SEQ ID NO: 10 and an expression vector comprising a polynucleotide comprising a sequence that encodes a light-chain variable region consisting of the amino acid sequence shown by SEQ ID NO: 4.

15. A method for producing an anti-human CTGF antibody or anti-human CTGF antibody fragment, the method comprising:
    (a) expressing an anti-human CTGF antibody or anti-human CTGF antibody fragment by culturing
    a host cell transformed with an expression vector comprising a polynucleotide comprising a sequence that encodes a heavy chain variable region consisting of the amino acid sequence shown by SEQ ID NO: 10 and a polynucleotide comprising a sequence that encodes a light chain variable region consisting of the amino acid sequence shown by SEQ ID NO: 4, or a host cell transformed with an expression vector comprising a polynucleotide comprising a sequence that encodes a heavy-chain variable region consisting of the amino acid sequence shown by SEQ ID NO: 10 and an expression vector comprising a polynucleotide comprising a sequence that encodes a light-chain variable region consisting of the amino acid sequence shown by SEQ ID NO: 4, to produce said anti-human CTGF antibody or anti-human CTGF antibody fragment; and (b) isolating said anti-human CTGF antibody or anti-human CTGF antibody fragment.

16. A host cell which is selected from the group consisting of:

a host cell transformed with an expression vector comprising a polynucleotide comprising a sequence that encodes a heavy chain consisting of the amino acid sequence shown by SEQ ID NO: 12 and a polynucleotide comprising a sequence that encodes a light chain consisting of the amino acid sequence shown by SEQ ID NO: 8; and a host cell transformed with an expression vector comprising a polynucleotide comprising a sequence that encodes a heavy chain consisting of the amino acid sequence shown by SEQ ID NO: 12 and an expression vector comprising a polynucleotide comprising a sequence that encodes a light chain consisting of the amino acid sequence shown by SEQ ID NO: 8.

17. A method for producing an anti-human CTGF antibody, the method comprising:

(a) expressing an anti-human CTGF antibody by culturing a host cell transformed with an expression vector comprising a polynucleotide comprising a sequence that encodes a heavy chain consisting of the amino acid sequence shown by SEQ ID NO: 12 and a polynucleotide comprising a sequence that encodes a light chain consisting of the amino acid sequence shown by SEQ ID NO: 8; or a host cell transformed with an expression vector comprising a polynucleotide comprising a sequence that encodes a heavy chain consisting of the amino acid sequence shown by SEQ ID NO: 12 and an expression vector comprising a polynucleotide comprising a sequence that encodes a light chain consisting of the amino acid sequence shown by SEQ ID NO: 8, to produce said anti-human CTGF antibody; and (b) isolating said anti-human CTGF antibody.

18. An expression vector comprising a polynucleotide comprising a sequence that encodes a heavy-chain variable region consisting of the amino acid sequence shown by SEQ ID NO: 10 and a polynucleotide comprising a sequence that encodes a light-chain variable region consisting of the amino acid sequence shown by SEQ ID NO: 4.

19. An expression vector comprising a polynucleotide comprising a sequence that encodes a heavy chain consisting of the amino acid sequence shown by SEQ ID NO: 12 and a polynucleotide comprising a sequence that encodes a light chain consisting of the amino acid sequence shown by SEQ ID NO: 8.

20. An anti-human CTGF antibody or anti-human CTGF antibody fragment, comprising a heavy-chain variable region comprising CDR1 consisting of amino acid sequence at position from 31 to 35 of SEQ ID NO: 10, CDR2 consisting of amino acid sequence at position from 50 to 66 of SEQ ID NO: 10, and CDR3 consisting of amino acid sequence at position from 99 to 108 of SEQ ID NO: 10, and a light-chain variable region comprising CDR1 consisting of amino acid sequence at position from 24 to 35 of SEQ ID NO: 4, CDR2 consisting of amino acid sequence at position from 51 to 57 of SEQ ID NO: 4, and CDR3 consisting of amino acid sequence at position from 90 to 98 of SEQ ID NO: 4.

21. The anti-human CTGF antibody or anti-human CTGF antibody fragment according to claim 20, comprising a heavy chain constant region which is a human Igγ1 constant region.

22. The anti-human CTGF antibody or anti-human CTGF antibody fragment according to claim 20, comprising a light chain constant region which is a human Igκ constant region.

23. The anti-human CTGF antibody or anti-human CTGF antibody fragment according to claim 20, comprising a heavy chain constant region which is a human Igγ1 constant region and a light chain constant region which is a human Igκ constant region.

24. The anti-human CTGF antibody fragment according to claim 20, wherein the fragment is a single-chain variable region fragment, Fab, Fab', or F(ab')$_2$.

25. The anti-human CTGF antibody or anti-human CTGF antibody fragment according to claim 20, wherein the antibody or the fragment is fused with another peptide or protein, or is modified with polyethylene glycol.

* * * * *

SEQUENCE LISTING

```
<160> NUMBER OF SEQ ID NOS: 14

<210> SEQ ID NO 1
<211> LENGTH: 357
<212> TYPE: DNA
<213> ORGANISM: Artificial Sequence
<220> FEATURE:
<223> OTHER INFORMATION: VH gene of anti-human CTGF antibody
```

<400> SEQUENCE: 1

```
caggtgcagc tggtgcagtc tggggctgag gtgaagaagc ctggggcctc agtgaaggtc      60
tcctgcaagg cttctggata caccttcacc ggctactata tgtattgggt gcgacaggcc     120
cctggacaag gcttgagtg gatgggatgg atcaaccctaacagtggtgg cacaaactat      180
tcacagaagt tcagggcag ggtcaccatg accagggaca cgtccatcag cacagcctac     240
atggagctga gcaggctgag atctgacgac acggccctgt attactgtgc gagagggagt     300
aagtggaact acccttttga ctactggggc cagggaaccc tggtcaccgt ctcctca       357
```

<210> SEQ ID NO 2
<211> LENGTH: 119
<212> TYPE: PRT
<213> ORGANISM: Artificial Sequence
<220> FEATURE:
<223> OTHER INFORMATION: VH of anti-human CTGF antibody

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ser Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Ser Lys Trp Asn Tyr Pro Phe Asp Tyr Trp Gly Gln Gly
            100                 105                 110

Thr Leu Val Thr Val Ser Ser
        115
```

<210> SEQ ID NO 3
<211> LENGTH: 327
<212> TYPE: DNA
<213> ORGANISM: Artificial Sequence
<220> FEATURE:
<223> OTHER INFORMATION: VL gene of anti-human CTGF antibody

<400> SEQUENCE: 3

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gaagggccac tggcatccca     180
gacaggttca gtggcagtgg gtctgggaca gacttcactc tcaccatcag cagactggag     240
cctgaagatt ttgtagtgta tttctgtcag cagtatgtca gcacaccgtg gacgttcggc     300
caagggacca aggtggaaat caaacgg                                         327
```

<210> SEQ ID NO 4
<211> LENGTH: 109
<212> TYPE: PRT
<213> ORGANISM: Artificial Sequence
<220> FEATURE:
<223> OTHER INFORMATION: VL of anti-human CTGF antibody

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Val Val Tyr Phe Cys Gln Gln Tyr Val Ser Thr Pro
                85                  90                  95

Trp Thr Phe Gly Gln Gly Thr Lys Val Glu Ile Lys Arg
            100                 105
```

<210> SEQ ID NO 5
<211> LENGTH: 1350
<212> TYPE: DNA
<213> ORGANISM: Artificial Sequence
<220> FEATURE:
<223> OTHER INFORMATION: H-chain gene of anti-human CTGF antibody

<400> SEQUENCE: 5

```
caggtgcagc tggtgcagtc tggggccgag gtgaagaagc tggggcctc agtgaaggtc      60
tcctgcaagg cttctggata caccttcacc ggctactata tgtattgggt gcgacaggcc    120
cctggacaag ggcttgagtg gatgggatgg atcaaccecta acagtggtgg cacaaactat    180
tcacagaagt ttcagggcag ggtcaccatg accaggggaca cgtccatcag cacagcctac    240
atggagctga gcaggctgag atctgacgac acggccctgt attactgtgc gagagggagt    300
aagtggaact acccttttga ctactggggc cagggaaccc tggtcaccgt ctcctcagcc    360
tccaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc ttagtagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgagctg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaatga                                    1350
```

```
<210> SEQ ID NO 6
<211> LENGTH: 449
<212> TYPE: PRT
<213> ORGANISM: Artificial Sequence
<220> FEATURE:
<223> OTHER INFORMATION: H-chain of anti-human CTGF antibody

<400> SEQUENCE: 6
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Gly | Tyr |
| | | | 20 | | | | | 25 | | | | | 30 | | |
| Tyr | Met | Tyr | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Asn | Pro | Asn | Ser | Gly | Gly | Thr | Asn | Tyr | Ser | Gln | Lys | Phe |
| | 50 | | | | | 55 | | | | | 60 | | | | |
| Gln | Gly | Arg | Val | Thr | Met | Thr | Arg | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Leu | Tyr | Tyr | Cys |
| | | | | 85 | | | | | 90 | | | | | 95 | |
| Ala | Arg | Gly | Ser | Lys | Trp | Asn | Tyr | Pro | Phe | Asp | Tyr | Trp | Gly | Gln | Gly |
| | | | 100 | | | | | 105 | | | | | 110 | | |
| Thr | Leu | Val | Thr | Val | Ser | Ser | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | 355 | | | | | 360 | | | | | 365 | | | |

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 7
<211> LENGTH: 648
<212> TYPE: DNA
<213> ORGANISM: Artificial Sequence
<220> FEATURE:
<223> OTHER INFORMATION: L-chain gene of anti-human CTGF antibody

<400> SEQUENCE: 7

```
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gaagggccac tggcatccca    180
gacaggttca gtggcagtgg gtctgggaca gacttcactc tcaccatcag cagactggag    240
cctgaagatt ttgtagtgta tttctgtcag cagtatgtca gcacaccgtg gacgttcggc    300
caagggacca aggtggaaat caaacggact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag              648
```

<210> SEQ ID NO 8
<211> LENGTH: 215
<212> TYPE: PRT
<213> ORGANISM: Artificial Sequence
<220> FEATURE:
<223> OTHER INFORMATION: L-chain of anti-human CTGF antibody

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Val Val Tyr Phe Cys Gln Gln Tyr Val Ser Thr Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 9
<211> LENGTH: 357
<212> TYPE: DNA
<213> ORGANISM: Artificial Sequence
<220> FEATURE:
<223> OTHER INFORMATION: VH gene of anti-human CTGF antibody

<400> SEQUENCE: 9
caggtgcagc tggtgcagtc tggggccgag gtgaagaagc tggggcctc agtgaaggtc      60 tcctgcaagg cttctggata caccttcacc ggctactata tgtattgggt gcgacaggcc    120
cctggacaag gcttgagtg gatgggatgg atcaacccta acagtggtgg cacaaactat    180
gcccagaagt ttcagggcag ggtcaccatg accagggaca cgtccatcag cacagcctac    240
atggagctga gcaggctgag atctgacgac acggccctgt attactgtgc gagagggagt    300
aagtggaact acccttttga ctactggggc cagggaaccc tggtcaccgt ctcctca       357

<210> SEQ ID NO 10
<211> LENGTH: 119
<212> TYPE: PRT
<213> ORGANISM: Artificial Sequence
<220> FEATURE:
<223> OTHER INFORMATION: VH of anti-human CTGF antibody

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Ser Lys Trp Asn Tyr Pro Phe Asp Tyr Trp Gly Gln Gly
            100                 105                 110

Thr Leu Val Thr Val Ser Ser
        115

<210> SEQ ID NO 11
<211> LENGTH: 1350
<212> TYPE: DNA
<213> ORGANISM: Artificial Sequence
<220> FEATURE:
<223> OTHER INFORMATION: H-chain of anti-human CTGF antibody

<400> SEQUENCE: 11

```
caggtgcagc tggtgcagtc tggggccgag gtgaagaagc ctggggcctc agtgaaggtc      60
tcctgcaagg cttctggata caccttcacc ggctactata tgtattgggt gcgacaggcc     120
cctggacaag gcttgagtg gatgggatgg atcaaccccta acagtggtgg cacaaactat     180
gcccagaagt ttcagggcag gtcaccatg accaggaca cgtccatcag cacagcctac     240
atggagctga gcaggctgag atctgacgac acggccctgt attactgtgc gagagggagt     300
aagtggaact accctttga ctactggggc cagggaaccc tggtcaccgt ctcctcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc ttagtagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 12
<211> LENGTH: 449
<212> TYPE: PRT
<213> ORGANISM: Artificial Sequence
<220> FEATURE:
<223> OTHER INFORMATION: H-chain of anti-human CTGF antibody

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Ser Lys Trp Asn Tyr Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 1050
<212> TYPE: DNA
<213> ORGANISM: Homo sapiens

<400> SEQUENCE: 13

```
atgaccgccg ccagtatggg ccccgtccgc gtcgccttcg tggtcctcct cgccctctgc      60
agccggccgg ccgtcggcca gaactgcagc gggccgtgcc ggtgcccgga cgagccggcg     120
ccgcgctgcc cggcgggcgt gagcctcgtg ctggacggct gcggctgctg ccgcgtctgc     180
gccaagcagc tgggcgagct gtgcaccgag cgcgaccct gcgaccccgca caagggcctc     240
ttctgtgact tcggctcccc ggccaaccgc aagatcggcg tgtgcaccgc caaagatggt     300
gctccctgca tcttcggtgg tacggtgtac cgcagcggag agtccttcca gagcagctgc     360
aagtaccagt gcacgtgcct ggacggggcg gtgggctgca tgcccctgtg cagcatggac     420
gttcgtctgc ccagccctga ctgccccttc ccgaggaggg tcaagctgcc cgggaaatgc     480
tgcgaggagt gggtgtgtga cgagcccaag gaccaaaccg tggttgggcc tgccctcgcg     540
gcttaccgac tggaagacac gtttggccca gacccaacta tgattagagc caactgcctg     600
gtccagacca cagagtggag cgcctgttcc aagacctgtg ggatgggcat ctccacccgg     660
gttaccaatg acaacgcctc ctgcaggcta gagaagcaga ccgcctgtg catggtcagg     720
ccttgcgaag ctgacctgga agagaacatt aagaagggca aaagtgcat ccgtactccc     780
aaaatctcca agcctatcaa gtttgagctt tctggctgca ccagcatgaa gacataccga     840
gctaaattct gtggagtatg taccgacggc cgatgctgca ccccccacag aaccaccacc     900
ctgccggtgg agttcaagtg ccctgacggc gaggtcatga agaagaacat gatgttcatc     960
aagacctgtg cctgccatta caactgtccc ggagacaatg acatctttga atcgctgtac    1020
tacaggaaga tgtacggaga catggcatga                                     1050
```

<210> SEQ ID NO 14
<211> LENGTH: 349
<212> TYPE: PRT
<213> ORGANISM: Homo sapiens

<400> SEQUENCE: 14

```
Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
```

```
                    180                 185                 190
Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
        210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
                260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
        290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
                340                 345
```